United States Patent [19]

Noguchi et al.

[11] Patent Number: 5,770,310
[45] Date of Patent: Jun. 23, 1998

[54] COMPOSITE FINE PARTICLES OF METAL OXIDES AND PRODUCTION THEREOF

[75] Inventors: Tamio Noguchi, Iwakishi-Fukushima; Yukitaka Watanabe, Iwaki, both of Japan

[73] Assignee: Merck Patent Gesellschaft Mit Beschrankter Haftung, Germany

[21] Appl. No.: 831,302

[22] Filed: Apr. 1, 1997

[30] Foreign Application Priority Data

Apr. 2, 1996 [JP] Japan ..................... 8-102046

[51] Int. Cl.⁶ ............... B32B 5/16; B05D 7/00
[52] U.S. Cl. ............. 428/403; 106/436; 106/439; 106/449; 427/214; 427/215; 427/372.2; 428/701
[58] Field of Search ............... 428/403, 701, 428/570; 427/212, 214, 215, 372.2; 106/436, 439, 449

[56] References Cited

U.S. PATENT DOCUMENTS 4,290,847  9/1981  Johnson et al. ............... 376/103
4,528,240  7/1985  Miyoshi et al. ............... 428/323
5,411,803  5/1995  George et al. ............... 428/403

OTHER PUBLICATIONS

Abstract of JP 72042502, Apr 1970.
Abstract of JP 6172149; Jun. 1994.
Abstract of JP 92005001; Jan. 1992.
Abstract of JP 2178219; Jul. 1990.
Abstract of JP 5330825; Dec. 1993.
Abstract of JP 93029363; Apr. 1993.

*Primary Examiner*—H. Thi Le
*Attorney, Agent, or Firm*—Millen, White, Zelano & Branigan, P.C.

[57] ABSTRACT

Composite fine particles of metal oxides containing titanium dioxide which produce a remarkable ultraviolet screening effect over the entire region of spectrum. Each particle is composed of a core and a surface layer, said core being composed of a nucleus formed from (a) titanium dioxide or (b) iron oxide or (c) a mixture of iron oxide and titanium dioxide and an outer layer of titanium dioxide, said surface layer being formed from metal oxides of magnesium and calcium.

14 Claims, 1 Drawing Sheet ic # COMPOSITE FINE PARTICLES OF METAL OXIDES AND PRODUCTION THEREOF

FIELD OF THE INVENTION

The present invention relates to composite fine particles of metal oxides, each particle being composed of a core and a surface layer, said core being composed of a nucleus and outer layer, the nucleus formed from (a) titanium dioxide or (b) iron oxide or (c) a mixture of iron oxide and titanium dioxide and the outer layer of titanium dioxide, said surface layer being formed from magnesium oxide and calcium oxide.

The present invention relates also to a process for producing said composite fine particles of metal oxides.

The present invention relates also to a cosmetic, paint, or plastic composition which contains said composite fine particles of metal oxides as an ultraviolet screening agent.

BACKGROUND OF THE INVENTION

Ultrafine particles of titanium oxide have long been in general use for cosmetics, paints, and plastics as an ultraviolet screening agent because of their high transparency and high absorption and scattering in the B region (290–320 nm) of ultraviolet rays. (See, for example, Japanese Patent Publication No. 42502/1972.) A new type of ultrafine particle of titanium oxide has recently been proposed (in Japanese Patent Laid-open No. 172149/1994). It is based on amorphous titanium oxide instead of the crystalline form. Despite such improvement, conventional products are made of titanium oxide alone and hence they suffer the disadvantage of taking on a pale, unhealthy color inherent in titanium oxide when put on the face.

Several means have been devised to overcome this disadvantage. They include the coating of titanium oxide with iron oxide (Japanese Patent Publication No. 5001/1992) and the introduction of iron oxide into crystals (Japanese Patent Laid-open Nos. 178219/1990 and 330825/1993). Such modification, however, makes fine particles of titanium oxide liable to agglomeration. Resulting agglomerates require a high shear force for re-pulverization at the time of incorporation into cosmetics. This adversely affects other ingredients in the cosmetics.

There has been proposed a pigment of a composite sol of titanium oxide and cerium oxide (in Japanese Patent Publication No. 29363/1993). The composite sol has limited application because it contains a medium for dispersing it. In addition, it is not thoroughly effective in screening the A region of ultraviolet rays (320–400 nm range, longer than the B region) which is said to damage the elastic properties of the skin.

SUMMARY OF THE INVENTION

In order to improve upon the properties of the above-mentioned known pigments, the inventors conducted extensive research culminating in the development of new composite fine particles of metal oxides which are superior in stability, color (not pale), transparency, easiness of powdering, and screening effect (for the A region of ultraviolet rays), particularly in comparison to the known particles discussed.

It is an object of the present invention to provide the following three kinds of composite fine particles of metal oxides.

(A) Composite fine particles of metal oxides having a particle diameter equal to or less than 0.5 µm, each particle comprising a core and a surface layer, said core being composed of a nucleus of titanium dioxide and an outer layer of titanium dioxide, said surface layer being formed from metal oxides of magnesium and calcium, with the amount of magnesium and calcium accounting for 2–20 wt % of the total particle weight (in terms of metal oxides) and the molar ratio of the amount of calcium to the amount of magnesium being 0.2–5 (in terms of metal oxide).

(B) Composite fine particles of metal oxides having a particle diameter equal to or less than 0.5 µm, each particle comprising a core and a surface layer, said core being composed of a nucleus of iron oxide and an outer layer of titanium dioxide, said surface layer being formed from metal oxide of magnesium and calcium, with the amount of iron oxide (in terms of $Fe_2O_3$) accounting for 2–20 wt % of the total particle weight, the amount of magnesium and calcium accounting for 2–20 wt % of the total particle weight (in terms of metal oxides), and the molar ratio of the amount of calcium to the amount of magnesium being 0.2–5 (in terms of metal oxide).

(C) Composite fine particles of metal oxides having a particle diameter equal to or less than 0.5 µm, each particle comprising a core and a surface layer, said core being composed of a nucleus of metal oxide mixture of iron oxide and titanium dioxide and an outer layer of titanium dioxide, said surface layer being formed from metal oxide of magnesium and calcium, with the amount of iron oxide (in terms of $Fe_2O_3$) accounting for 2–20 wt % of the total particle weight, the amount of magnesium and calcium accounting for 2–20 wt % of the total particle weight (in terms of metal oxides), and the molar ratio of the amount of calcium to the amount of magnesium being 0.2–5 (in terms of metal oxide).

It is another object of the present invention to provide the following three processes for producing said composite fine particles of metal oxides.

(a) A process for producing composite fine particles of metal oxides, said process comprising:

a first step of performing thermal hydrolysis on an aqueous solution of titanium tetrachloride by heating with stirring in the presence of a water-soluble polymeric substance, thereby preparing a colloid of titanium hydroxide;

a second step of adding dropwise to said colloid an aqueous solution of titanium tetrachloride and an alkaline aqueous solution simultaneously for neutralization and hydrolysis, thereby forming titanium dioxide hydrate and causing it to cover the particles of said colloid, the resulting product being a suspension of titanium dioxide hydrate particles;

a third step of preparing (1) an aqueous solution containing magnesium ions and calcium ions and (2) an aqueous solution of alkali metal hydroxide or alkali metal carbonate;

a fourth step of adding said aqueous solutions (1) and (2) simultaneously to said suspension prepared in said second step, thereby causing magnesium oxide hydrate or carbonate and calcium oxide hydrate or carbonate to coat the surface of the particles of said titanium dioxide hydrate; and a fifth step of collecting the solid product by filtration, which is followed by washing, drying, calcining, and powdering.

(b) A process for producing composite fine particles of metal oxides, said process comprising:

a first step of performing thermal hydrolysis on an aqueous solution of iron salt by heating with stirring in the presence of a water-soluble polymeric substance, thereby preparing a colloid of iron hydroxide;

a second step of adding dropwise to said colloid an aqueous solution of titanium tetrachloride and an alkaline aqueous solution simultaneously for neutralization and hydrolysis, thereby forming titanium dioxide hydrate and causing it to cover the particles of said colloid, the resulting product being a suspension of titanium dioxide hydrate coated iron oxide hydrate particles;

a third step of preparing (1) an aqueous solution containing magnesium ions and calcium ions and (2) an aqueous solution of alkali metal hydroxide or alkali metal carbonate;

a fourth step of adding said aqueous solutions (1) and (2) simultaneously to said suspension prepared in said second step, thereby causing magnesium oxide hydrate or carbonate and calcium oxide hydrate or carbonate to coat the surface of the said titanium dioxide hydrate coated iron oxide hydrate particles; and a fifth step of collecting the solid product by filtration, which is followed by washing, drying, calcining, and powdering.

(c) A process for producing composite fine particles of metal oxides, said process comprising:

a first step of performing thermal hydrolysis on a mixed aqueous solution of an iron salt and titanium tetrachloride by heating with stirring in the presence of a water-soluble polymeric substance, thereby preparing a mixed colloid of iron hydroxide and titanium hydroxide;

a second step of adding dropwise to said mixed colloid an aqueous solution of titanium tetrachloride and an alkaline aqueous solution simultaneously for neutralization and hydrolysis, thereby forming titanium dioxide hydrate and causing it to cover the particles of said mixed colloid, the resulting product being a suspension of titanium dioxide hydrate coated iron oxide hydrate and titanium oxide hydrate particles;

a third step of preparing (1) an aqueous solution containing magnesium ions and calcium ions and (2) an aqueous solution of alkali metal hydroxide or alkali metal carbonate;

a fourth step of adding said aqueous solutions (1) and (2) simultaneously to said suspension prepared in said second step, thereby causing magnesium oxide hydrate or carbonate and calcium oxide hydrate or carbonate to coat the surface of particles of said titanium dioxide hydrate containing iron oxide hydrate; and a fifth step of collecting the solid product by filtration, which is followed by washing, drying, calcining, and powdering.

It is another object of the present invention to provide a cosmetic, paint, or plastic composition which comprises containing therein composite fine particles of metal oxides as an ultraviolet screening agent.

Upon further study of the specification and appended claims, further objects and advantages of this invention will become apparent to those skilled in the art.

The composite fine particles of metal oxides pertaining to the present invention are characterized in that each particle is composed of a core and a surface layer, said core being composed of a nucleus formed from (a) titanium dioxide or (b) iron oxide or (c) a mixture of iron oxide and titanium dioxide and an outer layer of titanium dioxide, said surface layer being formed from metal oxide of magnesium and calcium.

In embodiment (a), the nucleus and outer layer of the core may be a unitary titanium dioxide core.

The fine particles of this construction are particularly effective in screening the A region as well as the B region of ultraviolet rays. In addition, those particles containing iron oxide are less liable to take on a pale color by its content. Hence they are particularly suitable for use as a raw material of cosmetics.

According to the present invention, the core is produced by any of the following processes.

Process (a): The core of titanium oxide is produced by performing thermal hydrolysis on an aqueous solution of titanium tetrachloride by heating with stirring in the presence of a water-soluble polymeric substance, thereby preparing colloid of titanium hydroxide, and subsequently coating the particles of said colloid with titanium dioxide hydrate.

Process (b): The core of iron oxide is produced by performing thermal hydrolysis on an aqueous solution of iron salt by heating with stirring in the presence of a water-soluble polymeric substance, thereby preparing colloid of iron hydroxide, and subsequently coating the particles of said colloid with titanium oxide.

Process (c): The core of iron oxide and titanium dioxide is produced by performing thermal hydrolysis on a mixed aqueous solution of iron chloride and titanium tetrachloride by heating with stirring in the presence of a water-soluble polymeric substance, thereby preparing mixed colloid of iron hydroxide and titanium hydroxide, and coating the particles of said colloid with titanium dioxide hydrate.

The first titanium dioxide as a raw material for the core may be commercial titanium dioxide of rutile type with a particle diameter of about 0.3 $\mu$m. However, the one obtained by the above-mentioned process (a) would give rise to uniform composite fine particles of metal oxides.

The water-soluble polymeric substance used in the present invention is exemplified by hydroxypropylcellulose (HPC), carboxypropylcellulose (CPC), and hydroxyethylcellulose (HEC). Its amount varies depending on its degree of polymerization; however, its maximum amount is only limited by its solubility in water. An adequate concentration (which is usually higher than 0.02% of water) should be established in consideration of economy and handling qualities.

The water-soluble polymeric substance helps the titanium hydroxide colloid to form the rutile crystals. It also helps to form rutile titanium dioxide for the core in the coating and calcining steps. It also contributes to uniform stable dispersion and growth of titanium hydroxide colloid and iron hydroxide colloid. An amount less than 0.02% is not enough to produce these effects. Conversely, an excess amount causes undesirable foaming.

The iron salt should be used in an amount (as $Fe_2O_3$) of 2–20 wt % of the total amount of the finished product. The iron salt is intended to reduce the pale color tone, and hence its amount should be selected according to the desired extent of pale color diminishing. An amount in excess of 20 wt % will have an adverse effect on transparency. An amount less than 2 wt % is not enough to eliminate the pale color. Any water-soluble iron salt may be used, for example its chloride, sulfate, or nitrate. Ferrous chloride, ferric chloride, ferrous sulfate, and ferric sulfate are desirable from the standpoint of availability and price.

According to the present invention, the core is formed by coating the nucleus with an outer layer of titanium dioxide. This step consists of adding dropwise to the colloid (which forms the nucleus) an aqueous solution of titanium tetrachloride and an alkaline aqueous solution simultaneously for neutralizing and hydrolysis, thereby forming titanium dioxide hydrate and causing it to cover the particles of said colloid. The titanium tetrachloride is used in the form of aqueous solution preferably with a concentration lower than 2.5 mol/L. An adequate concentration should be established in consideration of the growth of colloid particles (and hence productivity). For embodiment (a), it is not required that the core of titanium dioxide hydrate be provided with a separate outer layer of titanium oxide hydrate.

In this way there is obtained any one of three kinds of cores:
(i) the one which is composed of a nucleus of titanium dioxide hydrate and an outer layer of titanium dioxide hydrate.
(ii) the one which is composed of a nucleus of iron oxide hydrate and an outer layer of titanium dioxide hydrate.
(iii) the one which is composed of a nucleus of mixed oxide of iron and titanium and an outer layer of titanium dioxide hydrate.

The thus obtained core is coated with mixture of magnesium oxide hydrate and calcium oxide hydrate. This step consists of preparing (1) an aqueous solution containing magnesium ions and calcium ions and (2) an aqueous solution of alkali metal hydroxide or alkali metal carbonate, and adding these aqueous solutions simultaneously to the suspension of the metal oxide hydrate for the core. It is desirable to keep the pH value constant during addition of the aqueous solutions, so that the core particle is covered with a mixture of magnesium hydroxide and/or carbonate and calcium hydroxide and/or carbonate.

The aqueous solution (1) may be prepared from magnesium ions and calcium ions, which are not specifically restricted so long as they are water soluble. Usually they may be in the form of chloride, sulfate, or nitrate, such as, for example, magnesium chloride, magnesium nitrate, magnesium sulfate, magnesium acetate, calcium chloride, calcium nitrate, and calcium acetate, which are desirable because of their availability, low price, and water solubility. The concentration of the aqueous solution (1) is not specifically restricted so long as the two compounds are uniformly dissolved.

The alkali metal hydroxide for the aqueous solution (2) is not specifically restricted so long as it is soluble in water. Sodium hydroxide and potassium hydroxide are desirable because of their availability. The alkali metal carbonate for the aqueous solution (2) is not specifically restricted so long as it is soluble in water. Sodium carbonate, potassium carbonate, and ammonium carbonate are desirable because of their availability.

The aqueous solution (1) should contain magnesium ions and calcium ions such that the molar ratio of the amount of calcium to the amount of magnesium is in the range of 0.2–5 (in terms of metal oxide). If the molar ratio is lower than 0.2 or higher than 5, the resulting product would be poor in dispersibility and ultraviolet screening effect. The amount of magnesium and calcium (in terms of metal oxide) for coating should be in the range of 2–20 wt % of the total amount of the finished product. With an amount less than 2 wt %, it would be difficult to carry out powdering to give almost primary particles with a particle diameter equal to or less than 5 $\mu$m. Moreover, it would be difficult to obtain fine particles in a stable manner because the resulting fine particles are liable to re-agglomeration. Thus the resulting product would be poor in ultraviolet screening effect due to reflection in the A region of the spectrum of ultraviolet rays. Likewise, with an amount in excess of 20 wt %, the resulting product would be poor in ultraviolet screening effect.

The suspension obtained by the above-mentioned steps preferably undergoes solid-liquid separation by filtration which is followed preferably by water washing. To promote separation, it is permissible to add any known coagulant to the suspension. The coagulant would facilitate filtration and water washing and subsequent powdering. After separation, the solids are preferably dried and fired. The firing converts the surface-covering magnesium oxide hydrate and calcium oxide hydrate or the surface-covering magnesium carbonate and calcium carbonate partly into their respective metal oxides and partly into the titanates of their respective metals (i.e., magnesium titanite and calcium titanate) through solid-phase reaction with the titanium dioxide hydrate constituting the inner layer. Also, the titanium and iron oxide hydrates are converted to their oxides. The calcining temperature is preferably from 700°–1100° C. The higher the calcining temperature, the higher the rate at which titanium dioxide converts into rutile form and the magnesium titanite and calcium titanite are formed.

The results of X-ray diffractometry suggest that the fine particles after firing contain titanium dioxide of rutile type in a high ratio, and also contain magnesium titanate, calcium titanate, magnesium oxide, and calcium oxide. Therefore, it is believed that the composite fine particles of metal oxides pertaining to the present invention contain magnesium and calcium in the form of mixed oxide or double oxide in the surface layer and in the form of a mixture or complex of their respective titanates at the interface between the core and the surface layer, and that the titanium dioxide in the nucleus and core is present mostly in the form of rutile crystals owing to the magnesium and calcium which promote the conversion into rutile crystals.

The process of the present invention involves powdering, which may be accomplished, for example, by the use of an atomizer, jet mill, pulverizer, mixer, or the like. The easiness of powdering may vary depending on the amount and ratio of the magnesium and calcium compounds present in the surface layer. By selecting proper conditions for powdering, it is possible to obtain fine particles with a particle diameter equal to or less than 0.5 $\mu$m, preferably in the range of 0.5 to 0.03 $\mu$m. The resulting fine particles may be composed of primary particles and agglomerates.

The conversion of titanium dioxide in the core into rutile by the solid-phase reaction enhances the ultraviolet-screening effect.

The thus obtained composite fine particles of metal oxides pertaining to the present invention will find use as a raw material for cosmetics and paints. They produce the effect of screening ultraviolet rays, especially those in the A region. In addition, they are transparent and easily dispersible. Those which contain iron oxide are almost free of pale blue color and hence are particularly suitable for use as an ultraviolet screening agent for cosmetics.

The invention will be described in more detail with reference to the following examples, which are not intended to limit the scope of the invention.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding Japanese Application No. 96-102046, filed Apr. 2, 1996, are hereby incorporated by reference.

Figure 1:
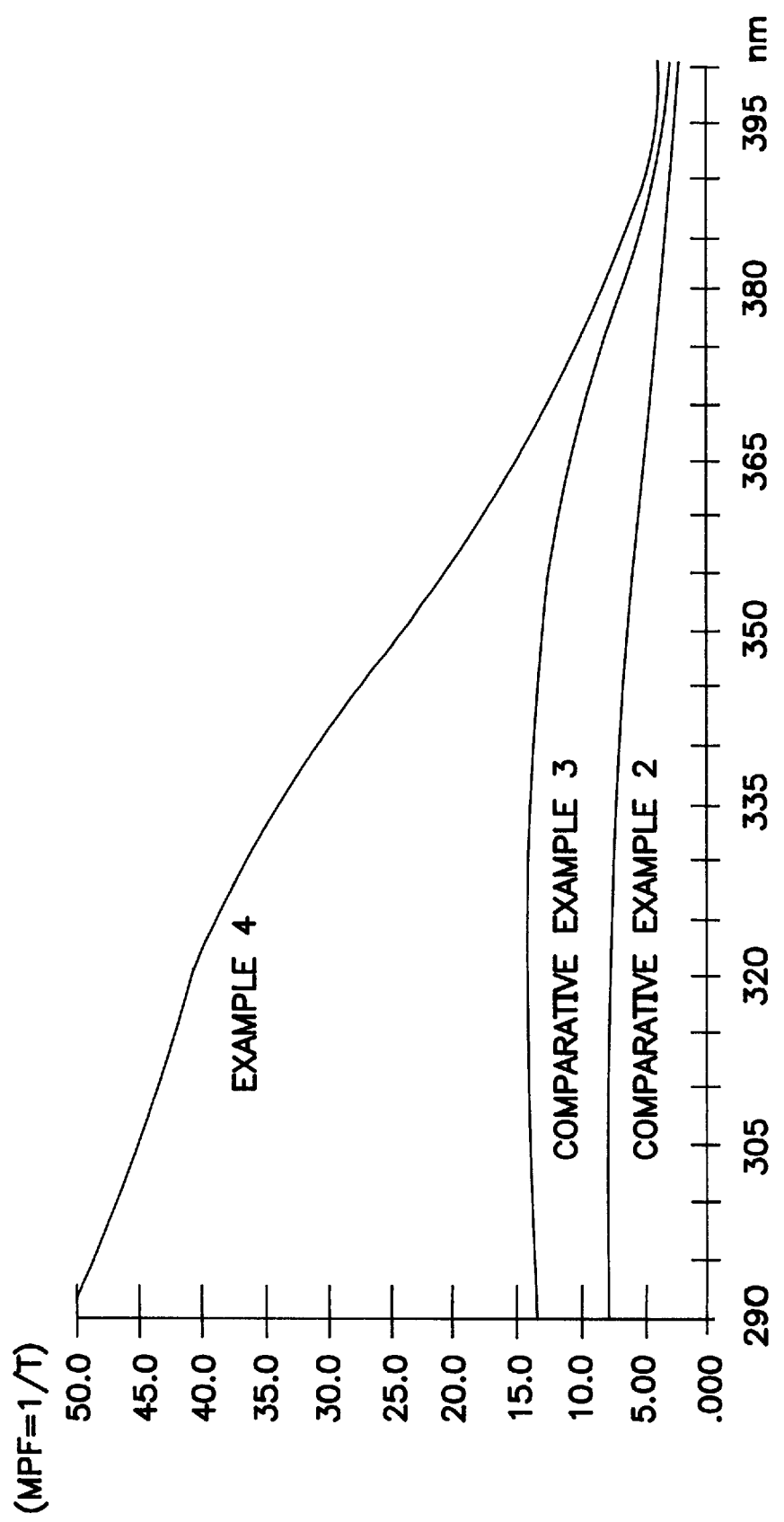
FIG. 1 is a diagram showing the ultraviolet screening effect of the samples of composite fine particles obtained in Example 4 and Comparative Examples 2 and 3.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

EXAMPLES

Example 1

An aqueous solution was prepared from both of 50 ml of titanium tetrachloride solution (an aqueous solution containing titanium tetrachloride in an amount of 2.18 mol/L in terms of $TiO_2$) and 0.30 g of hydroxypropylcellulose (a commercial reagent whose 2% aq. solution has a viscosity of 1000–4000 cps at 20° C.) by dissolution in 500 ml of water. The aqueous solution was heated to 60° C. with stirring so that the titanium tetrachloride underwent thermal hydrolysis. Thus there was obtained a white suspension containing titanium hydroxide colloid. The suspension was adjusted to pH 2.0 with a 32 wt % aqueous solution of sodium hydroxide. To the suspension was added dropwise (at a flow rate of 1.5 ml/min) 200 ml of said aqueous solution of titanium tetrachloride. During this step, the suspension was kept at pH 2.0 by adding said NaOH aqueous solution. The suspension was adjusted to pH 8.5 with a 30 wt % aqueous solution of potassium carbonate. To the suspension was added dropwise (at a flow rate of 1.0 ml/min) an aqueous solution containing both of 25 g of magnesium chloride hexahydrate and 13 g of calcium chloride dihydrate dissolved in 60 ml of water. During this step, the suspension was kept at pH 8.5 with said 30 wt % aqueous solution of potassium carbonate. After the completion of dropwise addition, the suspension was adjusted to pH 9.0 with the aqueous solution of potassium carbonate. To the resulting suspension was added 20 ml of aqueous solution containing 0.2 g of starch (as a coagulant). The coagulum was filtered off and the solids were washed with water and then dried. The dried product was powdered by using a blender and the resulting powder was calcined at 800° C. The calcined product was powdered again by using a blender. In this way there was obtained a white powder of fine particles.

Example 2

An aqueous solution was prepared from both of 50 g of 35 wt % aqueous solution of ferric chloride and 0.30 g of hydroxypropylcellulose (a commercial reagent whose 2% aq. solution has a viscosity of 1000–4000 cps at 20° C.) by dissolution in 500 ml of water. The aqueous solution was heated to 70° C. with stirring so that the ferric chloride underwent thermal hydrolysis. Thus there was obtained a brown suspension containing iron hydroxide colloid. The suspension was adjusted to pH 2.0 with a 32 wt % aqueous solution of sodium hydroxide. To the suspension was added dropwise (at a flow rate of 1.5 ml/min) 200 ml of titanium tetrachloride solution (an aqueous solution containing titanium tetrachloride in an amount of 2.18 mol/L in terms of $TiO_2$). During this step, the suspension was kept at pH 2.0 by adding said NaOH aqueous solution. The suspension was adjusted to pH 8.5 with a 30 wt % aqueous solution of potassium carbonate. To the suspension was added dropwise (at a flow rate of 1.0 ml/min) an aqueous solution containing both of 7.5 g of magnesium chloride hexahydrate and 7.5 g of calcium chloride dihydrate dissolved in 60 ml of water. During this step, the suspension was kept at pH 8.5 with said 30 wt % aqueous solution of potassium carbonate. After the completion of dropwise addition, the suspension was adjusted to pH 9.0 with the aqueous solution of potassium carbonate. To the resulting suspension was added 20 ml of aqueous solution containing 0.2 g of starch (as a coagulant). The coagulum was filtered off and the solids were washed with water and then dried. The dried product was powdered by using a blender and the resulting powder was calcined at 800° C. The calcined product was powdered again by using a blender. In this way there was obtained a light red powder of fine particles.

Example 3

An aqueous solution was prepared from 10 g of 35 wt % aqueous solution of ferric chloride and 50 ml of titanium tetrachloride solution (an aqueous solution containing titanium tetrachloride in an amount of 2.18 mol/L in terms of $TiO_2$) and 0.25 g of hydroxypropylcellulose (a commercial reagent whose 2% aq. solution has a viscosity of 1000–4000 cps at 20° C.) by dissolution in 500 ml of water. The aqueous solution was heated to 60° C. with stirring so that both of the ferric chloride and titanium tetrachloride underwent thermal hydrolysis. Thus there was obtained a white suspension containing both of iron hydroxide colloid and titanium hydroxide colloid. The suspension was adjusted to pH 2.0 with a 32 wt % aqueous solution of sodium hydroxide. To the suspension was added dropwise (at a flow rate of 1.5 ml/min) 200 ml of said aqueous solution of titanium tetrachloride. During this step, the suspension was kept at pH 2.0 by adding said NaOH aqueous solution. The suspension was adjusted to pH 8.5 with a 30 wt % aqueous solution of potassium carbonate. To the suspension was added dropwise (at a flow rate of 1.0 ml/min) an aqueous solution containing both of 7.5 g of magnesium chloride hexahydrate and 2.8 g of calcium chloride dihydrate dissolved in 60 ml of water. During this step, the suspension was kept at pH 8.5 with said 30 wt % aqueous solution of potassium carbonate. After the completion of dropwise addition, the suspension was adjusted to pH 9.0 with the aqueous solution of potassium carbonate. To the resulting suspension was added 20 ml of aqueous solution containing 0.2 g of starch (as a coagulant). The coagulum was filtered off and the solids were washed with water and then dried. The dried product was powdered by using a blender and the resulting powder was calcined at 800° C. The calcined product was powdered again by using a blender. In this way there was obtained a light red powder of fine particles.

Example 4

An aqueous solution was prepared from both of 50 ml of titanium tetrachloride solution (an aqueous solution containing titanium tetrachloride in an amount of 2.18 mol/L in terms of $TiO_2$) and 0.30 g of hydroxypropylcellulose (a commercial reagent whose 2% aq. solution has a viscosity of 1000–4000 cps at 20° C.) by dissolution in 500 ml of water. The aqueous solution was heated to 60° C. with stirring so that the titanium tetrachloride underwent thermal hydrolysis. Thus there was obtained a white suspension containing titanium hydroxide colloid. The suspension was adjusted to pH 2.0 with a 32 wt % aqueous solution of sodium hydroxide. To the suspension was added dropwise (at a flow rate of 1.5 ml/min) 200 ml of said aqueous solution of titanium tetrachloride. During this step, the suspension was kept at pH 2.0 by adding said NaOH aqueous solution. The suspension was adjusted to pH 8.5 with a 30 wt % aqueous solution of potassium carbonate. To the suspension was added dropwise (at a flow rate of 1.0 ml/min) an aqueous solution containing both of 12.5 g of magnesium chloride hexahydrate and 13.3 g of calcium chloride dihydrate dissolved in 60 ml of water. During this step, the suspension was kept at pH 8.5 with said 30 wt % aqueous solution of potassium carbonate. After the completion of dropwise addition, the suspension was adjusted to pH 9.0 with the aqueous solution of potassium carbonate. To the resulting suspension was added 20 ml of aqueous solution containing 0.2 g of starch (as a coagulant). The coagulum was filtered off and the solids were washed with water and then dried. The dried product was powdered by using a blender and the resulting powder was calcined at 800° C. The calcined product was powdered again by using a blender. In this way there was obtained a white powder of fine particles.

Comparative Example 1

An aqueous solution was prepared from both of 50 ml of titanium tetrachloride solution (an aqueous solution containing titanium tetrachloride in an amount of 2.18 mol/L in terms of $TiO_2$) and 0.25 g of hydroxypropylcellulose (a commercial reagent whose 2% aq. solution has a viscosity of 1000–4000 cps at 20° C.) by dissolution in 500 ml of water. The aqueous solution was heated to 60° C. with stirring so that the titanium tetrachloride underwent thermal hydrolysis. Thus there was obtained a white suspension containing titanium hydroxide colloid. The suspension was adjusted to pH 2.0 with a 32 wt % aqueous solution of sodium hydroxide. To the suspension was added dropwise (at a flow rate of 1.5 ml/min) 200 ml of said aqueous solution of titanium tetrachloride. During this step, the suspension was kept at pH 2.0 by adding said NaOH aqueous solution. The suspension was adjusted to pH 9.0 with a 30 wt % aqueous solution of potassium carbonate. To the suspension was added 20 ml of aqueous solution containing 0.2 g of starch (as a coagulant). The coagulum was filtered off and the solids were washed with water and then dried. The dried product was powdered by using a blender and the resulting powder was calcined at 800° C. The calcined product was powdered again by using a blender. In this way there was obtained a white powder of fine particles.

Comparative Example 2

An aqueous solution was prepared from both of 50 ml of titanium tetrachloride solution (an aqueous solution containing titanium tetrachloride in an amount of 2.18 mol/L in terms of $TiO_2$) and 0.25 g of hydroxypropylcellulose (a commercial reagent whose 2% aq. solution has a viscosity of 1000–4000 cps at 20° C.) by dissolution in 500 ml of water. The aqueous solution was heated to 60° C. with stirring so that the titanium tetrachloride underwent thermal hydrolysis. Thus there was obtained a white suspension containing titanium hydroxide colloid. The suspension was adjusted to pH 2.0 with a 32 wt % aqueous solution of sodium hydroxide. To the suspension was added dropwise (at a flow rate of 1.5 ml/min) 200 ml of said aqueous solution of titanium tetrachloride. During this step, the suspension was kept at pH 2.0 by adding said NaOH aqueous solution. The suspension was adjusted to pH 8.5 with a 30 wt % aqueous solution of potassium carbonate. To the suspension was added dropwise (at a flow rate of 1.0 ml/min) an aqueous solution containing 10 g of magnesium chloride hexahydrate dissolved in 60 ml of water. During this step, the suspension was kept at pH 8.5 with said 30 wt % aqueous solution of potassium carbonate. After the completion of dropwise addition, the suspension was adjusted to pH 9.0 with the aqueous solution of potassium carbonate. To the suspension was added 20 ml of aqueous solution containing 0.2 g of starch (as a coagulant). The coagulum was filtered off and the solids were washed with water and then dried. The dried product was powdered by using a blender and the resulting powder was calcined at 800° C. The calcined product was powdered again by using a blender. In this way there was obtained a white powder of fine particles.

Comparative Example 3

An aqueous solution was prepared from both of 50 ml of titanium tetrachloride solution (an aqueous solution containing titanium tetrachloride in an amount of 2.18 mol/L in terms of $TiO_2$) and 0.25 g of hydroxypropylcellulose (a commercial reagent whose 2% aq. solution has a viscosity of 1000–4000 cps at 20° C.) by dissolution in 500 ml of water. The aqueous solution was heated to 60° C. with stirring so that the titanium tetrachloride underwent thermal hydrolysis. Thus there was obtained a white suspension containing titanium hydroxide colloid. The suspension was adjusted to pH 2.0 with a 32 wt % aqueous solution of sodium hydroxide. To the suspension was added dropwise (at a flow rate of 1.5 ml/min) 200 ml of said aqueous solution of titanium tetrachloride. During this step, the suspension was kept at pH 2.0 by adding said NaOH aqueous solution. The suspension was adjusted to pH 8.5 with a 30 wt % aqueous solution of potassium carbonate. To the suspension was added dropwise (at a flow rate of 1.0 ml/min) an aqueous solution containing 5.2 g of calcium chloride dihydrate dissolved in 60 ml of water. During this step, the suspension was kept at pH 8.5 with said 30 wt % aqueous solution of potassium carbonate. After the completion of dropwise addition, the suspension was adjusted to pH 9.0 with the aqueous solution of potassium carbonate. To the suspension was added 20 ml of aqueous solution containing 0.2 g of starch (as a coagulant). The coagulum was filtered off and the solids were washed with water and then dried. The dried product was powdered by using a blender and the resulting powder was calcined at 800° C. The calcined product was powdered again by using a blender. In this way there was obtained a white powder of fine particles.

Table 1 below shows the compositions (calculated values) of the fine particles obtained in Examples 1 to 4 and Comparative Examples 1 to 3.

TABLE 1

| Example No. | $Fe_2O_3$ (wt %) | MgO + CaO (wt %) | MgO/CaO (molar ratio) |
|---|---|---|---|
| Example 1 | 0.0 | 18.5 | 1.40 |
| Example 2 | 18.2 | 9.2 | 0.74 |
| Example 3 | 3.6 | 5.4 | 1.94 |
| Example 4 | 0.0 | 14.9 | 0.69 |
| Comparative Example 1 | 0.0 | — | — |
| Comparative Example 2 | 0.0 | 4.5 | — |
| Comparative Example 3 | 0.0 | 4.5 | 0 |

Test Example (Evaluation of ultraviolet screening effect)

Each sample (5 g) of the fine particles obtained in Examples 1 to 4 and Comparative Examples 1 to 3 was added, together with 5 g of surface active agent, to 20 g of liquid paraffin heated to 60° C. To the liquid paraffin was further added 70 g of warm water. The liquid paraffin was emulsified by using a homogenizer. The resulting emulsion was applied to a tape for SPF measurement. The coating weight was 0.1 g per 64 $cm^2$. The SPF value and Erythemal UVA-Protection Factor were measured by using an SPF-290 analyzer produced by Optometrics Inc. The greater the SPF value, the more effective the specimen is in screening ultraviolet rays over the entire region of spectrum. The greater the Erythemal UVA-Protection Factor value, the more effective the specimen is in screening ultraviolet rays in the A region of spectrum. (See Fragrance Journal, vol. 9, p41, 1991.) If a specimen has high values for both SPF and Erythemal UVA-Protection Factor, it will produce a good effect of screening ultraviolet rays in the A region as well as the B region of spectrum. Table 2 shows the results of evaluation.

TABLE 2

| Example No. | SPF value | Erythemal UVA-ProtectionFactor value |
|---|---|---|
| Example 1 | 55.9 | 14.7 |
| Example 2 | 22.7 | 17.8 |
| Example 3 | 23.2 | 10.1 |
| Example 4 | 35.4 | 19.6 |
| Comparative Example 1 | 8.4 | 7.6 |
| Comparative Example 2 | 7.9 | 6.6 |
| Comparative Example 3 | 13.2 | 11.6 |

The samples of fine particles obtained in Example 4 and Comparative Examples 2 and 3 were tested for ultraviolet screening effect (in the region of 290–400 nm) using an SPE-290 analyzer. The results are shown in FIG. 1, in which the Monochro Protection Factor (1/T, T=transmittance) is plotted against the wavelength. It is apparent from the figure that all the samples tested produce remarkable screening effect over the entire region of spectrum of ultraviolet rays.

[Application Examples]

The following examples demonstrate the use of the composite fine particles in some application areas.

Application Example 1 (Compound powder)

Formulation

| Composite fine particles obtained in Example 1 | 25 g |
|---|---|
| Pigment | 5 g |
| Lanolin | 3 g |
| Isopropyl myristate | balance |
| Magnesium stearate | 2 g |
| Corn starch | 12 g |
| Talc | 50 g |

Application Example 2 (Paint)

Formulation

| Composition A (acryl-melamine resin) | |
|---|---|
| Acrydic 47-712 | 70 pbw |
| Superbeckamine G821-60 | 30 pbw |
| Composition B | |
| Composite fine particles obtained in Example 1 | 10 pbw |
| Pearlescent pigment | 10 pbw |
| Composition C (thinner for acryl-melamine resin) | |
| Ethyl acetate | 50 pbw |
| Toluene | 30 pbw |
| n-Butanol | 10 pbw |
| Solvesso #150 | 40 pbw |

A mixture of Composition A and Composition B was diluted with Composition C so that the resulting product has a viscosity (Ford cup #4, 12–15 seconds) suitable for spray coating. It was used to form a base coat layer by spray coating.

Application Example 3 (Plastic composition)

Formulation

| High-density polyethylene resin (pellet) | 100 pbw |
|---|---|
| Composite fine particles obtained in Example 1 | 1 pbw |
| Magnesium stearate | 0.1 pbw |
| Zinc stearate | 0.1 pbw |

The resulting dry blend was injection molded.

What is claimed is:

1. A composite fine particle of metal oxides having a particle diameter equal to or less than 0.5 μm, comprising a core and a surface layer, said core comprising a nucleus and outer layer wherein the nucleus comprises (A) titanium dioxide (B) iron oxide or (C) a mixture of titanium dioxide and iron oxide, and the outer layer comprises titanium dioxide, said surface layer comprising metal oxides of magnesium and calcium accounting for 2–20 wt % of the total particle weight in terms of metal oxide and, when the nucleus comprises iron oxide, the amount of iron oxide on $Fe_2O_3$ basis is 2–20% wt of the total particle weight.

2. The particle of claim 1, wherein the nucleus is titanium dioxide.

3. The particle of claim 2, wherein the titanium dioxide nucleus is obtained from titanium hydroxide colloid by thermal hydrolysis of an aqueous solution of titanium tetrachloride in the presence of a water-soluble polymeric substance.

4. The particle of claim 1, wherein the nucleus is iron oxide.

5. The particle of claim 4, wherein the iron oxide constituting the nucleus is obtained via iron hydroxide colloid by thermal hydrolysis of an aqueous solution of an iron salt in the presence of a water-soluble polymeric substance.

6. The particle of claim 1, wherein the nucleus is a mixture of titanium dioxide and iron oxide.

7. The particle of claim 6, wherein the mixture of iron oxide and titanium dioxide constituting the nucleus is obtained via a mixture of iron hydroxide colloid and titanium hydroxide colloid by thermal hydrolysis of a mixed aqueous solution of iron salt and titanium tetrachloride in the presence of a water-soluble polymeric substance.

8. The particle of claim 1, wherein the nucleous of said core comprises titanium dioxide and the titanium dioxide in the core is present mostly in the form of rutile crystals.

9. The particle of claim 1, wherein the surface layer further comprises magnesium titanate and/or calcium titanate.

10. The particle of claim 1, having a diameter of 0.5 to 0.03 μm.

11. A cosmetic, paint, or plastic composition containing therein composite fine particles of metal oxides according to claim 1 as a UV screening agent.

12. A process for producing a composite fine particle of metal oxides according to claim 1, said process comprising:

(a) performing thermal hydrolysis on an aqueous solution of (A) titanium tetrachloride (B) an iron salt or (C) titanium tetrachloride and an iron salt, by heating with stirring in the presence of a water-soluble polymeric substance, thereby preparing a colloid of titanium hydroxide or iron hydroxide or a mixed colloid of titanium hydroxide and iron hydroxide, (b) adding dropwise to said colloid an aqueous solution of titanium tetrachloride and an alkaline aqueous solution simultaneously for neutralization and hydrolysis, thereby forming titanium hydroxide and causing it to cover the particles of said colloid, the resulting product being a suspension of particles of titanium dioxide hydrate, titanium dioxide hydrate coated iron oxide hydrate, or titanium dioxide hydrate coated titanium and iron oxide hydrate;

(c) adding an aqueous solution (1) containing magnesium ions and calcium ions and an aqueous solution (2) of alkali metal hydroxide or alkali metal carbonate simultaneously to said suspension prepared in (b) thereby causing magnesium oxide hydrate and/or carbonate and calcium oxide hydrate and/or carbonate to coat the surface of the particles in the suspension; and (d) collecting the solid product by filtration, which is followed by washing, drying, calcining, and powdering.

13. The process of claim 12, wherein the water-soluble polymeric substance is hydroxypropylcellulose, carboxypropylcellulose, or hydroxyethylcellulose.

14. The process of claim 12, wherein the calcining is conducted at a temperature of 700°–1100° C.

* * * * *